United States Patent [19]

Harley et al.

[11] Patent Number: 5,453,557
[45] Date of Patent: Sep. 26, 1995

[54] PROCESSES FOR CONVERTING CHLORINATED BYPRODUCTS AND WASTE PRODUCTS TO USEFUL MATERIALS

[75] Inventors: A. Dale Harley; Michael T. Holbrook; David D. Smith; Mark D. Cisneros, all of Baton Rouge, La.; Larry N. Ito; Craig B. Murchison, both of Midland, Mich.

[73] Assignee: The Dow Chemical Company, Midland, Mich.

[21] Appl. No.: 227,812

[22] Filed: Apr. 14, 1994

Related U.S. Application Data

[63] Continuation-in-part of Ser. No. 112,042, Aug. 26, 1993, abandoned, which is a continuation-in-part of Ser. No. 955,173, Oct. 1, 1992, abandoned.

[51] Int. Cl.$^6$ .............................. C07C 1/26; C07C 21/04
[52] U.S. Cl. .......................... 585/641; 585/642; 570/216; 570/230
[58] Field of Search ..................... 585/641, 642, 585/733; 570/181, 189, 216, 230

[56] References Cited

U.S. PATENT DOCUMENTS

| | | | |
|---|---|---|---|
| 3,354,234 | 11/1967 | Hayden et al. | 260/636 |
| 3,789,020 | 1/1974 | Carter et al. | 252/442 |
| 3,892,818 | 7/1975 | Scharfe et al. | 423/481 |
| 4,083,809 | 4/1978 | De Thomas et al. | 252/457 |
| 4,379,076 | 4/1983 | Eberly, Jr. et al. | 252/439 |
| 4,585,891 | 4/1986 | Morris | 560/204 |
| 4,636,485 | 1/1987 | van der Smissen | 502/66 |
| 4,716,087 | 12/1987 | Ito et al. | 429/40 |
| 4,798,911 | 1/1989 | Lentz et al. | 568/747 |
| 4,818,368 | 4/1989 | Kalnes et al. | 208/50 |
| 4,895,995 | 1/1990 | James, Jr. et al. | 585/310 |
| 4,899,001 | 2/1990 | Kalnes et al. | 585/310 |
| 4,920,088 | 4/1990 | Kolts | 502/326 |
| 5,013,424 | 5/1991 | James et al. | 208/78 |

FOREIGN PATENT DOCUMENTS

| | | |
|---|---|---|
| 948211 | 5/1974 | Canada. |
| 1119203 | 3/1982 | Canada. |
| 0015665 | 2/1980 | European Pat. Off.. |
| 0253410 | 7/1987 | European Pat. Off.. |
| 0459463 | 5/1991 | European Pat. Off.. |
| 496446A1 | 7/1992 | European Pat. Off.. |
| 2460078 | 12/1974 | Germany. |
| 161240A3 | 12/1975 | Germany. |
| 235630 | 5/1986 | Germany. |
| 3510034 | 9/1986 | Germany. |
| 3804265 | 8/1989 | Germany. |
| 4012007 | 10/1991 | Germany. |
| 5231005 | of 0000 | Japan. |
| 15326 | 2/1981 | Japan. |
| 22081 | 1/1989 | Japan. |
| 5320076 | 12/1993 | Japan. |
| 94/22792 | 10/1994 | WIPO. |

OTHER PUBLICATIONS

"Conversion of 1,1,2,2-tetrachloroethane on $CuCl_2/Al_2O_3$ Catalyst", All–Union Institute of Scientific and Technical Information of the Academy of Sciences of USSR, No. 1896–78, Jun. 12, 1978.

Effects of Acidity & Metal Ensembles Size on the Coke Formation in Platinum/Nay & Platinum Copper/Nay by Methylcyclopentane Conversion; Z, Zhang, et al. Catalyst Deactivation pp. 727–733, 1991.

Hydrogenation of Toluene Over Platinum and Platinum–Copper Alloys in May; J. Bandiera et al 1988; Reuct. Kinet. Catal. Lett., vol. 37, pp. 373–377, 1988.

Monte Carlo Simulations of Supported Bimetallic Catalyst; John K. Shrohl & Terry S. King J. Catalysis, vol. 119, pp. 540–555, 1989.

Charaterization and Catalyst of Pt–Cu Clusters in Nay Giuliano Moretti, Wolfgang M. H. Sachtler J. Catalysis, 15, 205–216, 1984.

Hydrogen Chemisorption and Surface Composition of Silica–Supported Platinum–Copper Alloys James H. Anderson, Jr. et al; J. Calalysis, 1989; pp. 326–331.

Influence of Alloying Pt with Cu on the Reaction Mechanisms of Hydrocarbon Reforming Reactions; H. C. De Jongste; J. Catalysis, 63, pp. 395–403, 1980.

Absorption of CO on Pt–Cu Alloys.; F. J. C. M. Toolenaar et al; J. Catalysis, 64, pp. 110–115, 1980.

Co Oxidation Activity and XPS Studies of PT–Cu/y–A1203 Bimetallic Catalyst; P. C. Liao et al J. Catalysis, 74, pp. 307–316, 1982.

Role of Cu in the Deuterium Addition and Exchange of Propene Pd–Cu and Pt–Cu Alloy Shuichi et al; J. Catalysis, 119, pp. 300–310, 1989.

Chemisorption Complexes in the Reactions of Neohexane of Platinum–Copper Alloy Catalysts M. J. P. Botman et al; J. Catalysis, 68, pp. 9–16 (1981).

Cyclic Voltammetry of Supported "Cluster" Catalyst Containing Pt, Ru and Cu John Williams et al; Appl. Surf. Sci., 6, pp. 62–70, 1980.

The Dehalogenation of Haloaalkanes on $SiO_2$–supported Metals; Yasuhide et al; Bulletin of the Chemical Society of Japan, 45, 2319–2325, 1972.

*Primary Examiner*—P. Achutamurthy

[57] ABSTRACT

A process for the catalytic conversion of various chlorinated hydrocarbon byproducts and waste products especially to less chlorinated, useful or salable products, in which a chlorinated hydrocarbon feedstock containing two or more chlorines is reacted with hydrogen in the presence of a catalyst consisting essentially of an active hydrogenating metal component such as platinum in elemental or compound form, and a surface segregating metal component such as copper in elemental or compound form on a support.

27 Claims, No Drawings

PROCESSES FOR CONVERTING CHLORINATED BYPRODUCTS AND WASTE PRODUCTS TO USEFUL MATERIALS

This application is a continuation-in-part of U.S. patent application Ser. No. 08/112,042, now abandoned, filed Aug. 26, 1993, which is a continuation-in-part of U.S. patent application Ser. No. 07/955,173, filed Oct. 1, 1992, now abandoned.

The present invention relates generally to processes for converting chlorinated hydrocarbons to less chlorinated products and to the catalysts used in such processes.

European Patent Application EP 0496446A describes the preparation of chlorotrifluoroethylene and trifluoroethylene from 1,1,2-trichloro-1,2,2-trifluoroethane via a catalyst comprised of copper and a Group VIII or noble metal (palladium and platinum being preferred) on a carbon support. Several prior publications address the same conversion and describe the same or different catalysts, see, for example EP 0253410B, EP 0355907B and EP 0459463A. None of these publications describes or suggests, however, that other halogenated feedstocks might be suitably catalytically converted to less halogenated and more useful or more salable materials, and in particular none of these references suggest that the catalysts described therein might be useful outside of the fluorocarbon art.

A seemingly separate course of development has occurred with respect to the class of chlorinated hydrocarbon feedstocks which are exclusive of the chlorofluorocarbon feedstocks (and which will henceforth and for simplicity be referred to generically as the chlorinated hydrocarbon feedstocks).

With respect to such chlorinated hydrocarbon feedstocks, a number of references may be found which relate to the conversion of a chlorinated alkane feedstock to a less chlorinated alkene product. For example, EP 015665 describes the conversion of 1,1,2-trichloroethane to ethylene or to vinyl chloride via a catalyst including a noble metal chloride, an alkali metal chloride, iron chloride and optionally copper chloride on a silica or alumina support. An earlier Japanese patent publication JP 77/31005 which is referenced in the EP 015665 publication relates to the same overall process, but employs a catalyst of palladium chloride, copper chloride and an alkali metal chloride on a support.

U.S. Pat. No. 2,886,605 to McClure et al. describes processes for reducing the chlorine or bromine content of halohydrocarbons containing one or both of these halogens via a cuprous halide on porous active alumina catalyst. Specifically contemplated are processes for converting 1,2-dichloropropane to propylene and hydrogen chloride, for converting perchloroethylene to trichloroethylene, and for converting 1,1,2-trichloroethane to vinyl chloride.

British patent GB 1,400,529 to Scharfe broadly relates to processes for converting byproduct and waste "hydrocarbon chlorides" to "chlorine-free hydrocarbons" via a rhodium-containing catalyst, and specifically describes the conversion of 1,2-dichloropropane to propane, as well as describing the conversion of chloropropane to propylene. Combinations of rhodium with other metals or metal compounds are contemplated, those being named including palladium, platinum, ruthenium, iridium, iron, cobalt, nickel, copper, gold, vanadium, chromium, molybdenum or tungsten, and the salts, hydroxides, oxides or carboxylates of the alkali and alkaline earth metals.

Other known references are specifically addressed to the conversion of 1,2-dichloropropane (hereafter, PDC) to the less saturated, less chlorinated propylene.

In German Patent Publication No. 235,630 Al, for example, PDC is converted to propylene in a catalytic gas phase reaction at temperatures ranging from 170 degrees Celsius to 450 degrees Celsius. The catalyst is described as an activated carbon which has been treated with a suspension of iron oxides and/or iron oxide hydrates, and then dried at temperatures in the range of 0 degrees to 200 degrees Celsius.

Other methods described in this publication include the conversion (preferably at 180–250 degrees Celsius) in the presence of hydrogen and of a rhodium catalyst of PDC to propylene, the dechlorination at normal temperatures of PDC to a mixture (9:1) of propylene and chloropropylene in the presence of a pure titanium catalyst, and the reductive dehalogenation with sodium sulfide and a phase transfer catalyst of chlorinated hydrocarbons to alkylenes. The production of alkylenes from halogenated phosphonate esters under the influence of sulfur and olefinating agents containing phosphorus is also described.

Still other known references involve the conversion of a chlorinated alkane feedstock such as the aforementioned 1,2-dichloropropane to a corresponding less chlorinated alkane. The aforementioned British patent GB 1,400,529 to Scharfe is illustrative, and has been summarized previously.

U.S. Pat. Nos. 4,818,368 to Kalnes et al., 4,899,001 to Kalnes et al., and 5,013,424 to James, Jr. et al. are closely related in describing processes for the hydrogenation of halogenated hydrocarbons in the presence of hydrogenating metal or mixed hydrogenating metal catalysts involving a combination of Group VIB and Group VIII metals. "Hydrogenation" in these patents is contemplated as including dehalogenation and olefin saturation in addition to other processes, such as desulfurization, denitrification, oxygenate conversion and hydrocracking.

A common objective in each of these various references is the conversion of a chlorinated hydrocarbon feedstock which may be formed as a byproduct or waste material of another useful process into a more directly useful or more salable product or products. A prime example is the conversion of 1,2-dichloropropane or PDC (as a significant byproduct of the chlorohydrin process for producing propylene oxide) to propylene for recycle to a chlorohydrin process for producing propylene oxide, for use in the preparation of allyl chloride or for other uses and benefits.

Applicants' inventive processes are similarly focused, and provide for the catalytic conversion of various less-desired chlorinated hydrocarbon feedstocks to corresponding, less-chlorinated products in commercially substantial proportions (that is, at yields (defined as the selectivity to a corresponding, less-chlorinated product multiplied by the conversion, on an hydrogen chloride- and hydrogen-free basis) of a given product of at least about 10 percent, but more preferably at least about 20 percent and most preferably at least about 30 percent), in which a chlorinated hydrocarbon feedstock containing two or more chlorines is reacted with hydrogen in the presence of a supported catalyst which consists essentially of (and preferably consists entirely of) an active hydrogenating metal component in elemental or compound form with a surface segregating metal component, also in elemental or compound form. The desired product(s) is (are) then conventionally separated from those which are not desired, and may be further processed in a conventional, known manner to be placed in condition for an appropriate use or for sale.

Briefly speaking, three classes of reactions are contemplated with these catalysts:

(a) the conversion of a chlorinated alkane containing two or more chlorines to reaction products including a corresponding less chlorinated alkane in a commercially substantial proportion, as an example, 1,2-dichloropropane (or PDC) to propane;

(b) the conversion of a chlorinated alkene containing two or more chlorines to a corresponding less chlorinated alkane, for example, trichloroethylene to ethane; and (c) the conversion of a chlorinated alkane containing two or more chlorines to reaction products including a corresponding less chlorinated alkene, for example, PDC to propylene.

"Less chlorinated", as should be clear from the examples given above of reaction classes (a) through (c), embraces still-chlorinated hydrocarbons as well as hydrocarbons having no remaining chlorine atoms associated therewith.

The present invention thus embraces the catalytic conversion of a wide array of possible chlorinated hydrocarbon starting materials to corresponding less chlorinated reaction products, including less chlorinated reaction products of the same or different degrees of saturation. A preferred application is in the conversion of chlorinated alkane feedstocks to corresponding, less-chlorinated alkenes. Examples of preferred chlorinated alkane feedstocks and their corresponding preferred, less chlorinated alkene products include: PDC and propylene; 1,2,3-trichloropropane and allyl chloride, propylene; 1,1,1,2-tetrachloroethane to vinylidene chloride and ethylene; and, 1,1,2-trichloroethane and vinyl chloride.

The principles and theory behind surface segregation in catalytic alloys, and the experimental techniques which may be employed to determine surface segregation in such alloys are known in the art, as shown for example in Hegde and Sinha, "ESCA Study of Metals and Alloys" Applied Spectroscopy Reviews, Vol. 19, No. 1, pp. 1-25. Based on prior experimental observations, the general rule is expressed in the referenced publication that with respect to bimetallic alloys, the metal having the lower heat of sublimation and larger atomic radius will segregate preferentially on the surface of the alloy as compared to the bulk. The surface segregating behaviors of ternary systems and the effects of external agencies/catalyst environment and treatment are also discussed.

Applicants have found by the present invention that a catalyst consisting essentially of an active hydrogenating metal component and of a surface segregating metal component can be effectively used for a variety of feedstocks and processes in categories (a) through (c) above, and that the selectivity of the catalyst to a given less-chlorinated product over a less-favored such product can be controlled through a knowledge of the surface segregating tendencies of a selected hydrogenating metal component and a selected surface segregating metal component in a given environment and application.

More particularly and by way of example, Applicants have found that a given, preferred supported bimetallic catalyst consisting essentially of, and more preferably consisting entirely of, an active hydrogenating metal (such as from Groups VIb or VIII of the Periodic Table) and of a second metal determined by experimental surface analysis techniques or previously known to preferentially surface segregate in the presence of the hydrogenating metal, can be made to selectively convert a chlorinated alkane feedstock such as PDC to either propane or propylene depending on the relative concentrations of the two metals.

The surface segregation behaviors of a number of alloys have already been studied and documented, as noted above with reference to the Hegde and Sinha article. In broad terms, however, the catalysts which are preferred for use in the processes of the present invention consist essentially of one or more active Group VIII hydrogenating metals in elemental or compound form, with one or more metals in elemental or compound form which will surface segregate in combinations with the one or more selected Group VIII metals. It is presently contemplated that the surface segregating component may preferably be selected from among the metals (in elemental or compound form) of Groups IB, IIB, IIIA or IIIB, IVA or IVB VA or VB, VIA or VIIA, or from the remaining Group VIII metals which will surface segregate with a selected Group VIII hydrogenating metal component (the aforementioned groups corresponding to those provided in the Periodic Table of the Elements, as published by Sargent-Welch Scientific Company, Skokie, Ill. USA as Catalog No. S-18806 (1979)).

Presently preferred catalysts will consist essentially of a selected Group IB surface segregating metal component in elemental or compound form and a selected, active Group VIII hydrogenating metal component in elemental or compound form on a support.

More preferably, the catalysts employed in the processes of the present invention will consist entirely of a Group IB surface segregating metal with an active, Group VIII hydrogenating metal on a support.

The Group VIII and Group IB metal combinations which are generally favored include platinum (in elemental or compound form) and copper or silver (in elemental or compound form, with copper being preferred to silver) for processes in class (c), and platinum/gold or platinum/silver (platinum/gold being more preferred for classes (a) and (b). Other Group VIII and Group IB metals can be included in other embodiments, but more preferably, the Group VIII and Group IB metals in a given catalyst will consist simply of platinum and copper in their elemental or compound forms on the one hand or platinum and gold on the other.

The proportions and amounts of platinum or other selected active Group VIII hydrogenating metal and copper or other selected Group IB surface segregating metal in these catalysts will vary depending on the catalyst's intended use and on the method of catalyst preparation which is employed, but in general terms and for a catalyst prepared by solution impregnation (including more particularly coimpregnation) of the carrier, the selected Group IB metal can be anywhere from about 0.01 to about 20 percent by weight (on an elemental basis) of the catalyst, with platinum or another selected Group VIII metal comprising from about 0.01 to about 5.0 percent by weight (also on an elemental basis) of the catalyst.

More preferably, the Group IB metal will be from about 0.05 to about 15 percent by weight of the catalyst (on an elemental basis) and the Group VIII metal will be from about 0.03 to about 3.0 percent by weight of the catalyst. Most preferably, the Group IB metal can be from about 0.1 to about 10 percent by weight of the catalyst (on an elemental basis) and the Group VIII metal will be from about 0.05 to about 1.0 percent by weight of the catalyst.

The support in each of these various catalysts can be any of the known conventional inert supports, but is preferably silica or carbon, with carbon being most preferred. The carbon is preferably a high surface area carbon, for example, a carbon having a specific surface area in an unimpregnated condition of about 200 $m^2/g$ or more, especially about 400 m²/g or more, and most especially about 600 m²/g or more.

An example of a commercially-available carbon which has been found to be well-suited for use in various of the contemplated processes is a coal-based carbon produced by Calgon Carbon Corporation under the designation "BPLF3", and may generally be characterized as having a specific surface area of 1100 m²/g to 1300 m²/g, a pore volume of 0.7 to 0.85 cm³/g, and an average pore radius of 12.3 to 14 angstroms. Based on an X-ray fluorescence analysis of this carbon, a typical bulk composition of the BPLF3 carbon has been determined to be as follows (by weight percent): silicon, 1.5 percent; aluminum, 1.4 percent; sulfur, 0.75 percent; iron, 0.48 percent; calcium, 0.17 percent; potassium, 0.086 percent; titanium, 0,059 percent; magnesium, 0,051 percent; chlorine, 0,028 percent; phosphorus, 0,026 percent; vanadium, 0,010 percent; nickel, 0.0036 percent; copper, 0.0035 percent; chromium, 0.0028 percent; and manganese, 0.0018 percent (the remainder being carbon).

Other carbons may be preferable for specific processes within the broader classes (a) through (c) above. For example, either a coconut-based carbon such as produced by Calgon Carbon Corporation under the designation PCB (having a published specific surface area of from 1150 to 1250 m²/g and a pore volume of 0.72 cm³/g) or a wood-based carbon such as produced by Calgon Carbon Corp. as WSIV Special carbon (having a published or reported specific surface area of 1400 m²/g, and a pore volume of 1.25 cm³/g) is preferred for the conversion of 1,2,3-trichloropropane to propylene because of the lower rate of catalyst deactivation observed with the use of these catalyst supports in this process application as compared to the aforementioned BPLF3 carbon.

The reaction conditions preferred for the different processes of the present invention will again vary, depending for example on the particular catalyst and the particular chlorinated hydrocarbon feedstock involved, or whether the process is to be conducted in the gas phase or liquid phase.

In general, however, in the gas phase processes reaction pressures can range from atmospheric up to about 1500 psig, with temperatures of from about 100 deg. C. to about 350 deg. C., residence times of from about 0.25 seconds to about 180 seconds, and hydrogen/chlorinated alkane or alkene feed ratios ranging on a molar basis from about 0.1:1 to about 100:1.

More preferably, reaction pressures will range from about 5 psig to about 500 psig, with temperatures of from about 180 deg. C. to about 300 deg. C., residence times of from about 0.5 seconds to about 120 seconds, and hydrogen/chlorinated alkane or alkene feed ratios of from about 0.5:1 to about 20:1.

Most preferably, reaction pressures in the gas phase processes will range from about 40 psig to about 300 psig, with temperatures of from about 200 deg. C. to about 260 deg. C., residence times of from about 1 second to about 90 seconds, and hydrogen/chlorinated alkane or alkene molar feed ratios of from about 0.75:1 to about 6:1.

In the liquid phase processes (which can be conducted in a batchwise or continuous manner, as desired), it is anticipated that the reaction pressures will generally range from atmospheric up to about 3000 psig, at temperatures of from about 25 degrees Celsius to about 350 degrees Celsius, residence times of from about 1 to about 30 minutes and hydrogen to chlorinated alkane or alkene molar feed ratios of from about 0.1:1 to about 100:1.

Of the classes of processes described above, the conversion of a chlorinated alkane feedstock including two or more chlorines to reaction products including (in a commercially substantial proportion) a corresponding less chlorinated alkene is particularly of interest, and of greater interest still is the direct conversion of such a feedstock to a corresponding non-chlorinated alkene. A preferred example is the gaseous-phase reaction of 1,2-dichloropropane or PDC with hydrogen to form reaction products including propylene in a commercially-substantial proportion.

For this particular process, the catalyst is preferably a supported bimetallic platinum/copper catalyst of from about 0.01 to about 5.0 percent by weight of platinum (calculated on an elemental basis) and from about 0.01 to about 15 percent by weight of copper (also calculated on an elemental basis) on a carbon support having a specific surface area of at least about 200 m²/g. More preferably, the catalyst includes from about 0.10 to about 3.0 percent by weight of platinum and from about 0.05 to about 5 percent by weight of copper, and the carbon support has a specific surface area of at least about 500 m²/g. Most preferably, the catalyst includes from about 0.20 to about 1.0 percent by weight of platinum and from about 0.1 to about 2.0 percent by weight of copper, and the carbon support has a specific surface area of at least about 800 m²/g. A particularly preferred carbon is the above-described BPLF3 carbon.

Preferably the catalyst for this process (and for other contemplated processes within the chlorinated alkane to less-chlorinated alkene class) will have been pretreated by exposure to a chloride source, for example, hydrogen chloride, to improve initial selectivity to propylene over propane, and to make the product stream immediately useful in an allyl chloride process (wherein impurity propane in the feed can react with chlorine to produce 1-chloropropane, which because of a similarity in boiling points to allyl chloride is difficult to separate therefrom), for example, or to minimize venting in a propylene oxide process of any propane in the product stream fed or recycled to the propylene oxide process. In this regard, catalysts of the present invention which have been impregnated, dried and reduced under hydrogen have been observed to produce propane with decreasing selectivity and propylene with increasing selectivity over time. The initial chloride source pretreatment substantially reduces, however, the amounts of venting or downstream processing involved in making use of the product stream in a propylene oxide process or allyl chloride process, respectively.

Catalysts that have been pretreated by exposure to a chloride source and not reduced, or which have been merely dried and started up (and which have been in essence treated with hydrogen chloride in situ on start up), have been observed to produce the least amount of propane initially, albeit with a substantial penalty in conversion. For this reason, it is considered that it will generally be preferable to both reduce and pretreat (by exposure to a chloride source) a given catalyst, as opposed to reducing the catalyst solely, or not reducing the catalyst at all in favor of chloride-source pretreatment or treatment with HCl in situ on startup.

It will also be preferred in the context of this process (and further, in each of the various processes contemplated herein) to employ hydrogen chloride in the feed to reduce coking and catalyst deactivation rates, as exemplified below. Preferably the rate of conversion loss experienced in the processes of the present invention is no more than about 0.03 percent per hour, and especially no more than about 0.01 percent per hour.

The pressure under which the PDC to propylene reaction is conducted preferably ranges from atmospheric pressure to about 1500 psig, more preferably from about 5 psig to about 500 psig, and most preferably from about 50 psig to about 300 psig. The temperature will preferably be from about 100 deg. C. to about 350 deg. C., more preferably will be from about 180 deg. C. to about 300 deg. C., and most preferably will be from about 200 deg. C. to about 260 deg. C. Preferred residence times will be from about 0.25 seconds to about 180 seconds, more preferably will be from about 1.0 seconds to about 20 seconds, and most preferably will be from about 5 to about 15 seconds. Hydrogen to 1,2-dichloropropane feed ratios will preferably be (again, on a molar basis) from about 0.1:1 to about 100:1. More preferably, the hydrogen to PDC feed ratios will be from about 0.3:1 to about 10:1, and most preferably from about 0.5:1 to about 3:1. Preferably this process will on a commercial-scale further include a recycle stream comprised of any unreacted PDC and 2-chloropropane (as a by-product of the reaction), although as suggested above the amount of 2-chloropropane that is produced is preferably minimized by reduction and chloride source pretreatment of the Pt/Cu bimetallic catalyst.

Those skilled in the art will of course recognize that the processes of the present invention may be combined with other, perhaps conventional processes if expedient for the handling and disposition of various chlorinated feedstocks, and particularly for the expedient processing of streams including a mixture of chlorinated alkane or alkene byproducts. Thus, for example, a process of the present invention for converting chlorinated alkanes to less-chlorinated, useful alkenes could be employed with a preceding process for saturating chlorinated alkenes from within a mixed stream of chlorinated alkanes and chlorinated alkenes, for example a process of the type disclosed in the earlier-cited U.S. Pat. Nos. 4,818,368 to Kalnes et al., 4,899,001 to Kalnes et al., and 5,013,424 to James, Jr. et al.

ILLUSTRATIVE EXAMPLES

The present invention is more particularly illustrated by the examples which follow hereafter. In Examples 1–10, a number of catalyst preparations were evaluated for converting 1,2-dichloropropane to selected reaction products, for example propylene. Several parameters were measured and/or calculated for purposes of comparison, including PDC conversion (100 minus the mol percent of PDC in the test reactor effluent, excluding unreacted hydrogen and the hydrogen chloride produced by the reaction), selectivity to a given component (mols of component divided by mols PDC converted, multiplied by 100), liquid hourly space velocity (in $hr^{-1}$, the volume of liquid PDC fed per hour to the reactor divided by the packed bed volume of catalyst in the reactor), and catalyst productivity (on a basis of kilograms of propylene produced per hour per cubic meter of catalyst used).

For each example in Examples 1–10, PDC was converted to the selected reaction products by flowing hydrogen and PDC in the gas phase over a given catalyst to be evaluated. Liquid PDC was pumped via a piston pump through 1/16th inch (1.6 mm) (O.D.) nickel tubing to a Monel™ alloy (Huntington Alloys, Inco Alloys International, Inc.) gas sample cylinder packed with glass beads (unless specifically noted, all fittings and tubing were of Monel™ alloy). The 1/16th inch tubing extended to the center of the sample cylinder, with the sample cylinder being heated to a vaporization temperature of 110 degrees Celsius by electrical heat tracing. A thermocouple was used to monitor the skin temperature of the sample cylinder.

The flow of the hydrogen feed stream was controlled by a pre-calibrated mass flow controller. The desired flow of hydrogen was passed through the heated sample cylinder, where mixing of the gaseous PDC and hydrogen occurred. The mixed gases were then passed into a charged Monel™ tubular reactor (.0.75 in. (1.9 cm) O.D., 18 inches (45.7 cm.) in length) heated by ceramic lined electric elements to a desired reaction temperature.

The catalyst (1.2 cubic centimeters) was in each case charged into the reactor between 3 mm glass beads, and placed in the middle of the reactor. The catalyst was thereafter dried under a flow of nitrogen for one hour at 130 degrees Celsius, and then reduced the catalyst under a 5:1 molar ratio of flowing nitrogen and hydrogen. In reducing the catalyst, the temperature was ramped up from 130 to 220 degrees Celsius at 3 degrees per minute, and then held at 220 degrees for a total reducing cycle time of about 2 hours.

Upon reaction of the mixed hydrogen and PDC in the reactor at a prescribed reaction temperature, the effluent from the reactor passed to a gas sampling valve, which provided gaseous aliquots for online gas chromatographic analysis in a Hewlett-Packard Model 5890 Series II gas chromatograph (Hewlett-Packard Company). The gas chromatograph was equipped with a flame ionization detector, and used 30 meter by 0.53 millimeter (I.D.) 100 percent methyl silicone/fused silica and 30 meter by 0.53 millimeter (I.D.) porous polymer-lined fused silica columns to separate the various reaction products. Response factors were conventionally determined by injections of gravimetrically-prepared standards of the individual reaction products. These response factors were applied in conjunction with individual peak areas and the total mols of all reaction products to determine the mol percents of individual components in the reactor effluent, and the selectivity to individual reaction products as described above.

EXAMPLE 1

For this example a bimetallic platinum-copper catalyst was prepared on a carbon support for comparison to platinum on a carbon support alone, to copper on a carbon support alone, and to the carbon support alone.

For the platinum-copper catalyst, an aqueous $H_2PtCl_6$ stock solution was prepared by dissolving 3.179 grams of $H_2PtCl_6 \cdot 6H_2O$ (J. T. Baker, Inc.; Baker Analyzed Grade, 37.6 percent Pt) in 100.00 mL of deionized and distilled water. 0.381 grams of $CuCl_2$ (Aldrich Chemical Company, Inc., 99.999 percent purity) were placed in a 250 mL Erlenmeyer flask, and 8.305 grams of the $H_2PtCl_6$ stock solution were added with swirling to dissolve the $CuCl_2$. The solution was then diluted with 42.64 grams of deionized, distilled water and swirled. 40.04 grams of Calgon BPLF3 activated carbon (6×16 mesh, Calgon Carbon Corp., Pittsburgh, Pa.) were added to the flask, and the flask was agitated rapidly so that the carbon carrier was evenly coated with the aqueous Pt/Cu solution. The catalyst preparation was dried in an evaporating dish in air at ambient temperatures for 18 hours, and then further dried in an oven in air at 120 degrees Celsius for 2 hours before being charged to the reactor and reduced. The resulting catalyst was comprised of 0.25 percent by weight of platinum (on an elemental basis) and 0.45 percent by weight of copper (also on an elemental basis).

Similar methods of preparation were used to make catalysts of 0.48 percent by weight of copper on the Calgon BPL F3 activated carbon support (omitting the chloroplatinic acid solution), and of 0.25 percent by weight of platinum on the same activated carbon (omitting the CuCl$_2$ from the process).

Reactions were run at various reaction temperatures on the apparatus described above with separate charges of each of these catalysts, as well as running reactions at various temperatures with an unimpregnated Calgon BPLF3 activated carbon support as a test for reactivity of the support.

Each of the catalysts was loaded into the 18 inch (45.7 cm.) long tubular reactor described above, using about 1.2 cubic centimeters of catalyst. The liquid hourly space velocity (LHSV) was 1.25, and the hydrogen and PDC were fed to the reactor at a molar ratio of 6.0:1. Reactor temperatures, PDC conversions, productivities, and individual product selectivities for the runs with these catalysts are shown in Table 1 below. Propylene yields for the two runs with the bimetallic platinum/copper catalyst were thus 30.1 percent (for the 220 degree Celsius reaction temperature, or (30.64× 98.16)/100), and 67.4 percent (for the 250 degree Celsius reaction temperature, or (70.53×95.5)/100).

TABLE 1

| Catalyst | T(°C.) | PDC Conversion | SELECTIVITY (%) | | | | | | Productivity (kg/m$^3$ · hr) |
| --- | --- | --- | --- | --- | --- | --- | --- | --- | --- |
| | | | Allyl Chloride | 1-CPE[a] | C$_3$H$_6$[b] | C$_3$H$_8$[c] | 2-CPA[d] | 1-CPA[e] | |
| 0.48 Cu//C | 220 | 4.32 | 30.09 | 56.49 | 13.19 | 0 | 0 | 0 | 3.2 |
| | 250 | 5.65 | 22.28 | 45.60 | 32.12 | 0 | 0 | 0 | 9.6 |
| | 280 | 11.29 | 13.11 | 46.50 | 34.81 | 0 | 0 | 0 | 20.8 |
| | 310 | 27.86 | 6.17 | 49.61 | 33.52 | 0 | 1.54 | 0 | 49.6 |
| 0.25 Pt/C | 220 | 23.07 | 0.17 | 0.09 | 12.31 | 86.78 | 0.17 | 0.39 | 14.4 |
| | 250 | 62.06 | 0.02 | 0.05 | 7.54 | 91.70 | 0.26 | 0.37 | 25.6 |
| 0.25 Pt/0.45 Cu//C | 220 | 30.64 | 0 | 0.46 | 98.16 | 0 | 1.06 | 0.20 | 160.0 |
| | 250 | 70.53 | 0 | 0.50 | 95.50 | 0 | 3.68 | 0.32 | 358.4 |
| Calgon BPLF3 carbon | 220 | 2.46 | 5.55 | 39.16 | 54.51 | 0 | 0 | 0 | 8.0 |
| | 230 | 3.44 | 4.00 | 39.28 | 56.33 | 0 | 0 | 0 | 11.2 |
| | 240 | 4.78 | 3.47 | 41.78 | 54.67 | 0 | 0 | 0 | 14.4 |
| | 250 | 6.93 | 2.79 | 45.99 | 52.54 | 0 | 0 | 0 | 19.2 |

[a]1-CPE = 1-Chloropropene
[b]C$_3$H$_6$ = Propylene
[c]C$_3$H$_8$ = Propane?
[d]2-CPA = 2-Chloropropane
[e]1-CPA = 1-Chloropropane

EXAMPLES 2–6

In Examples 2–6, platinum-copper catalysts were prepared which used the same activated carbon support as in Example 1. The catalysts were each prepared and reduced as in Example 1, except that the catalysts for these examples used different amounts of platinum and copper (both on an elemental basis).

In the runs with each of these catalysts, 1.2 cubic centimeter charges of a given catalyst were employed in the 18 inch (45.7 cm.) Monel™ reactor, and the hydrogen to PDC feed ratio on a molar basis was set at 5:1 (rather than the 6:1 ratio seen in Example 1). Liquid hourly space velocities and reaction temperatures were varied. The results of these runs are shown in Table 2:

TABLE 2

| Catalyst | T(°C.) | LHSV[a] | PDC Conversion | SELECTIVITY (%) | | | | Productivity (kg/m$^3$ · hr) |
| --- | --- | --- | --- | --- | --- | --- | --- | --- |
| | | | | C$_3$H$_6$[b] | C$_3$H$_8$[c] | 2-CPA[d] | 1-CPE[e] | |
| 0.50 Pt/12.3 Cu//C | 250 | 0.30 | 36.7 | 77.7 | 8.9 | 9.5 | 3.9 | 35.2 |
| 0.28 Pt/3.42 Cu//C | 250 | 0.30 | 87.0 | 73.8 | .07 | 18.2 | 7.2 | 100.8 |
| | 250 | 0.60 | 59.0 | 82.3 | <.01 | 11.6 | 5.8 | 139.2 |
| | 250 | 0.90 | 43.4 | 86.4 | <.01 | 7.6 | 5.8 | 153.6 |
| 0.10 Pt/3.30 Cu//C | 250 | 0.30 | 51.5 | 86.1 | <.01 | 7.4 | 6.3 | 56.0 |
| 0.25 Pt/0.45 Cu//C | 220 | 1.25 | 30.4 | 98.8 | <.01 | 0.8 | 0.3 | 161.6 |
| | 250 | 1.25 | 63.4 | 96.8 | <.01 | 2.5 | 0.7 | 323.2 |
| 0.49 Pt/0.88 Cu//C | 220 | 1.25 | 38.3 | 93.4 | 0.6 | 4.3 | 0.6 | 193.6 |
| | 220 | 2.50 | 22.7 | 97.8 | 0.3 | 1.2 | 0.5 | 240.0 |
| | 240 | 2.50 | 43.2 | 96.4 | 0.2 | 2.4 | 0.5 | 451.2 |
| | 260 | 2.50 | 65.4 | 95.6 | 0.2 | 3.6 | 0.6 | 678.4 |

[a]LHSV = Liquid Hourly Space Velocity
[b]C$_3$H$_6$ = Propylene
[c]C$_3$H$_8$ = Propane
[d]2-CPA = 2-Chloropropane
[e]1-CPE = 1-Chloropropene

EXAMPLE 7

The catalyst prepared for this Example included palladium as the active hydrogenating metal component instead of platinum, as well as including the copper of previous examples.

In making the bimetallic palladium-copper catalyst of this example, 0.393 grams of $PdCl_2$ (Aldrich Chemical Company, Inc., 99.999% purity) was dissolved in 2 mL of 12M hydrochloric acid (HCl) and diluted to 25.00 mL in a volumetric flask with distilled, deionized water. 0.097 grams of $CuCl_2$ (Aldrich Chemical Company, Inc., 99.999% purity) was placed in a 50 mL Erlenmeyer flask, and 1.435 grams of the prepared $H_2PdCl_4$ stock solution was added with swirling to the flask containing the $CuCl_2$. When the $CuCl_2$ had dissolved, the resulting solution was diluted with 11.00 grams of deionized, distilled water and swirled.

10.00 grams of Calgon BPLF3 activated carbon (6×16 mesh, Calgon Carbon Corp.) were then added with agitation to coat the carbon evenly with solution, and the catalyst thus prepared was dried in air at ambient temperatures for 18 hours. The catalyst, which comprised 0.13 percent by weight of palladium on an elemental basis and 0.45 percent by weight of copper on an elemental basis on the activated carbon support, was then further air-dried in an oven at 120 degrees Celsius for 2 hours and reduced as described previously.

le;2qThree runs were conducted sequentially with this catalyst in the apparatus and according to the general procedure set forth just prior to Example 1 above, using a single 1.2 cubic centimeter charge of catalyst in the tubular reactor. The results from these runs are shown in Table 3 below, and suggest or show that a palladium/copper catalyst though useful is considerably less active than the previous platinum/copper catalyst (0.25 Pt/0.45 Cu//C) of equimolar proportions for the conversion of PDC to propylene.

TABLE 3

| Catalyst | T(°C.) | LHSV[a] | $H_2$/PDC | PDC Conversion | SELECTIVITY (%) $C_3H_6$[b] | $C_3H_8$[c] | 2-CPA[d] | 1-CPE[e] | Productivity (kg/m$^3$ · hr) |
|---|---|---|---|---|---|---|---|---|---|
| 0.13 Pd/0.45 Cu//C | 220 | 1.25 | 5 | 3.5 | 94.8 | <.01 | <.01 | 4.7 | 17.6 |
|  | 240 | 1.25 | 5 | 8.3 | 93.0 | <.01 | 0.5 | 5.8 | 41.6 |
|  | 240 | 1.25 | 2.5 | 9.2 | 91.5 | <.01 | 1.2 | 6.3 | 46.4 |

[a]LHSV = Liquid Hourly Space Velocity
[b]$C_3H_6$ = Propylene
[c]$C_3H_8$ = Propane
[d]2-CPA = 2-Chloropropane
[e]1-CPE = 1-Chloropropene

TABLE 4

| Catalyst | T(°C.) | LHSV[a] | $H_2$/PDC | PDC Conversion | SELECTIVITY (%) $C_3H_6$[b] | $C_3H_8$[c] | 2-CPA[d] | 1-CPE[e] | Productivity (kg/m$^3$ · hr) |
|---|---|---|---|---|---|---|---|---|---|
| 0.253 Ir/0.45 Cu//C | 220 | 1.25 | 5 | 33.3 | 67.9 | 30.2 | 1.7 | 0.2 | 123.2 |
|  | 220 | 1.25 | 2.5 | 38.8 | 68.0 | 27.8 | 4.0 | 0.3 | 140.8 |
|  | 250 | 1.25 | 5 | 74.8 | 63.0 | 33.2 | 3.7 | 0.1 | 256.0 |

[a]LHSV = Liquid Hourly Space Velocity
[b]$C_3H_6$ = Propylene
[c]$C_3H_8$ = Propane
[d]2-CPA = 2-Chloropropane
[e]1-CPE = 1-Chloropropene

TABLE 5

| Catalyst | T(°C.) | LHSV[a] | $H_2$/PDC | PDC Conversion | SELECTIVITY (%) $C_3H_6$[b] | $C_3H_8$[c] | 2-CPA[d] | 1-CPE[e] | Productivity (kg/m$^3$ · hr) |
|---|---|---|---|---|---|---|---|---|---|
| 0.29 Pt/0.75 Ag//C | 220 | 1.25 | 5 | 25.5 | 41.6 | 58.1 | 0.2 | <.01 | 57.6 |
|  | 220 | 1.25 | 2.5 | 27.2 | 60.9 | 38.5 | 0.5 | 0.1 | 89.6 |
|  | 220 | 1.25 | 1.25 | 22.9 | 81.0 | 17.7 | 1.0 | 0.3 | 100.8 |

[a]LHSV = Liquid Hourly Space Velocity
[b]$C_3H_6$ = Propylene
[c]$C_3H_8$ = Propane
[d]2-CPA = 2-Chloropropane
[e]1-CPE = 1-Chloropropene

TABLE 6

| Catalyst | T(°C) | LHSV[a] | H$_2$/PDC | PDC Conversion | SELECTIVITY (%) | | | | Productivity (kg/m · hr) |
|---|---|---|---|---|---|---|---|---|---|
| | | | | | C$_3$H$_6$[b] | C$_3$H$_8$[c] | 2-3PA[d] | 1-3PE[e] | |
| 0.24 Pt/1.37 Au//C | 220 | 1.25 | 5 | 21.5 | 6.8 | 93.0 | 0.2 | <.01 | 8.0 |

[a] LHSV = Liquid Hourly Space Velocity
[b] C$_3$H$_6$ = Propylene
[c] C$_3$H$_8$ = Propane
[d] 2-3PA = 2-Chloropropane
[e] 1-3PE = 1-Chloropropene

EXAMPLE 8

The catalyst for the sample runs in this example was comprised of 0.25 percent by weight of iridium (on an elemental basis) and 0.45 percent by weight of copper (again, on an elemental basis) on the same activated carbon support used in previous examples.

The iridium-copper catalyst was prepared via a stock solution of IrCl$_4$, by dissolving 0.911 grams of IrCl$_4$.xH$_2$O (53.4 percent iridium) in 4.988 grams of 0.1 M HCl solution in a 50.00 mL volumetric flask, and diluting this solution to 50.00 mL with deionized, distilled water.

0.095 grams of CuCl$_2$ (Aldrich Chemical Company, Inc., 99.999% purity) were placed in a 50 mL Erlenmeyer flask, and 2,553 grams of the IrCl$_4$ stock solution were added with swirling to dissolve the CuCl$_2$. This solution was diluted with 10.00 grams of deionized, distilled water. 10.00 grams of Calgon BPLF3 activated carbon (6×16 mesh) were added to the flask, and the flask agitated thoroughly to ensure that the activated carbon was evenly coated with the aqueous solution of IrCl$_4$ and CuCl$_2$. The catalyst made in this fashion, with 0.25 percent by weight of iridium (elemental basis) and 0.45 percent by weight of copper (elemental basis) on activated carbon, was air-dried as in previous examples, that is, at ambient temperature for 18 hours and then in an oven at 120 degrees Celsius for another 2 hours, and then reduced.

Three runs were conducted with the catalyst in the apparatus and according to the procedures described previously, with 1.2 cubic centimeter charges of catalyst being charged to the reactor for each set of reaction conditions. The remaining reaction parameters and the results of the runs are as indicated in Table 4 above.

These results suggest or show that the iridium/copper catalyst is generally less selective for converting PDC to propylene than a like-proportioned platinum/copper catalyst.

EXAMPLE 9

The catalyst tested in this example comprised 0.29 percent by weight on an elemental basis of platinum and 0.75 percent by weight of silver (as the surface segregating metal component of the catalyst) on the Calgon activated carbon, and was prepared first by making an aqueous stock solution from 0.048 grams of Pt(NH$_3$)$_4$(NO$_3$)$_2$ 0.116 grams of silver nitrate, and 12.43 grams of distilled, deionized water in a 50 mL Erlenmeyer flask. The same activated carbon as used in previous examples was then added (at 9.68 grams) to the flask containing the stock solution, and the flask agitated and the catalyst dried as in previous examples. A single 1.2 cubic centimeter charge (weighing 500.1 milligrams) of the catalyst was placed in the reactor dried and reduced, then tests were conducted sequentially with this catalyst at several hydrogen to PDC molar feed ratios.

The results from the testing are shown in Table 5 above.

EXAMPLE 10

For this example an aqueous H$_2$PtCl$_6$.H$_2$O stock solution was prepared by dissolving 3.179 grams of H$_2$PtCl$_6$.6H$_2$O (J. T. Baker Inc., Baker Analyzed Grade, 37.6 percent Pt) in 100.00 mL of distilled, deionized water. A portion (0.995 grams) of this stock solution was added with swirling to a 50 mL Erlenmeyer flask containing 0.134 grams of HAuCl$_4$.3H$_2$O (Aldrich Chemical Co., Inc., ACS purity) until the HAuCl$_4$.3H$_2$O was dissolved. The solution was diluted with 5.42 grams of distilled, deionized water, and then 4.79 grams of the same activated carbon used in previous examples were added to the flask with sufficient agitation to coat the carbon fully with the solution.

The catalyst was air-dried, again as in previous examples, at ambient temperatures for 18 hours and in an oven at 120 degrees Celsius for 2 hours. The catalyst thus prepared comprised 0.24 percent by weight of platinum (on an elemental basis) and 1.37 percent by weight of the gold surface segregating component (on an elemental basis) on the activated carbon support. These loadings correspond in terms of molar ratio to the 0.25 Pt/0.45 Cu catalyst of Example 1, and permit a direct comparison of the effectiveness of gold and copper in these catalyst combinations. The same proportions were observed in the other catalysts exemplified herein, that is, palladium and iridium were used in the same molar ratios as platinum in any of the platinum catalysts, and silver, gold and copper were used in the same molar ratios in the various catalysts as well.

A 1.2 cubic centimeter charge (again, about 500 mg in weight) of the catalyst was placed in the test reactor for drying, reduction and evaluation. The results of the single run conducted with this platinum/gold catalyst are summarized above in Table 6, and indicate that although some propylene is produced with this particular platinum/gold catalyst the dominant product is propane.

EXAMPLES 11–12

Examples 11–12 below focus on the dechlorination of 1,2,3-trichloropropane and 1,1,2-trichloroethane, respectively, over a supported platinum/copper catalyst of the present invention, with the catalyst having been prepared according to the method of Example 1 above.

In each instance, the feedstock was pumped via a high pressure syringe pump through 1.6 mm (O.D.) (1/16 inch) Monel™ nickel alloy tubing (unless specifically noted below all of the components, tubing and fittings of the test reactor apparatus were also made of Monel™ nickel alloy (Huntington Alloys, Inco Alloys International, Inc.)) into a packed sample cylinder serving as a feed evaporator.

The 1/16th inch tubing extended almost to the center of the packed cylinder, which was heated to a vaporizing temperature of 180 degrees Celsius using electrical heat tracing. Vaporization of the feedstock was accomplished in the feed line, so that the feedstock was superheated when combined with the hydrogen feed stream. Thermocouples were used to monitor the skin temperature of the feed evaporator and the temperature of the gas exiting the feed evaporator, and the temperature of the feed evaporator was controlled by computer.

The hydrogen feed stream was metered to a preheater using a Model 8249 linear mass flow controller from Matheson Gas Products, Inc. Secaucus, N.J., with the preheater consisting of a packed sample cylinder wrapped with electrical heat tracing. Thermocouples were used to monitor both the skin temperature of the preheater and the temperature of the gas exiting the preheater. The preheater temperature was set and maintained at 140 degrees Celsius.

Vaporized feedstock exiting the evaporator was mixed with the hydrogen gas from the preheater in a 2 foot (0.61 meter) long section of 1/4 inch (0.64 cm) tubing maintained at a temperature of 140 degrees Celsius. The mixed gases then were passed into and reacted within a tubular reactor (1/2 inch (1.27 cm) O.D., 12 inches (30.5 cm) in length) located within an aluminum block heated by a cartridge heater and regulated via a computer.

The catalyst charge (0.6 grams in each of Examples 11–) was generally placed in the tubular reactor over a glass wool support contained in the center of the reactor tubing. The catalyst was then covered with a plug of glass wool.

The catalyst was dried for from 8 to 24 hours at 150 degrees Celsius under a nitrogen purge. The catalyst was thereafter reduced by passing hydrogen through the reactor at a flow rate of 34 mL/minute for 24 hours, and the reactor temperature was lowered to the temperature setpoint of the particular catalyst run. The reactor temperature and hydrogen gas flow were allowed to equilibrate for about 1 hour before the liquid feedstock flow was started into the apparatus.

After reacting the feedstock and hydrogen in the vapor phase in the tubular reactor thus prepared, the products from the reaction were passed to a gas sampling valve, which provided gaseous aliquots for online gas chromatographic analysis in a Hewlett-Packard Model 5890 Series II gas chromatograph (Hewlett-Packard Company). The gas chromatograph was equipped with a flame ionization detector, and used 30 meter by 0.53 millimeter (I.D.) 100 percent methyl silicone/fused silica and 30 meter by 0.53 millimeter (I.D.) porous polymer-lined fused silica columns to separate the various reaction products. Response factors were conventionally determined by injections of gravimetrically-prepared standards of the individual reaction products. These response factors were applied in conjunction with individual peak areas and the total mols of all reaction products to determine the mol percents of individual components in the reactor effluent, and the selectivity to individual reaction products.

The feedstocks, conditions and results of Examples 11–12 are reported in Table 7 below:

TABLE 7

| Catalyst | Feed | T(°C.) | H2/Feed | Residence Time(s) | Conversion (%) | Products & Selectivities (%)[c] |
|---|---|---|---|---|---|---|
| 0.25 Pt/0.50 Cu//C | 1,2,3TCPa[a] | 180 | 16.9 | 8.6 | 98 | 78% $C_3H_6$, 10% $C_3H_8$ |
| | | 220 | 6.6 | 5.7 | 50 | 62% allyl chloride, 20% $C_3H_6$ |
| | 1,1,2TCEta[b] | 250 | 5.0 | 2.1 | 99 | 44% $C_2H_4$, 40% vinyl chloride, 15% $C_2H_6$ |

[a] = 1,2,3TCPa = 1,2,3-trichloropropane
[b] = 1,1,2TCEta = 1,1,2-trichloroethane
[c] = Balance to 100% are miscellaneous hydrocarbons

EXAMPLES 13–17

The experimental method and apparatus of Examples 11–12 above were employed (except as indicated below) in these Examples for determining the effects on the rate of catalyst deactivation in converting 1,2,3-trichloropropane to propylene of adding hydrogen chloride (HCl) to a 1,2,3-trichloropropane feed, and of omitting HCl from the feed but using a different wood- or coconut-based carbon support.

Bimetallic platinum/copper alloy catalysts were prepared for these examples in the ratios indicated in Table 8 below, by dissolving $H_2PtCl_6 \cdot 6H_2O$ (J. T. Baker, Inc.; Baker Analyzed Grade, 37.6 percent Pt) in deionized and distilled water. An amount of $CuCl_2$ (Aldrich Chemical Company, Inc., 99.999 percent purity) was placed in a 250 mL Erlenmeyer flask, and the $H_2PtCl_6$ stock solution was added with swirling to dissolve the $CuCl_2$. The solution was then diluted with deionized, distilled water and swirled. An activated carbon (Calgon BPLF3 carbon, 6×16 mesh, Calgon Carbon Corp., Pittsburgh, Pa. for the runs with HCl in the feed, Calgon PCB brand coconut-based activated carbon or Calgon WSIV Special wood-based activated carbon) was added to the flask, and the flask was agitated rapidly so that the carbon carrier was evenly coated with the aqueous Pt/Cu solution.

The various catalysts were charged to the reactor and dried under flowing nitrogen at 90 cubic centimeters per minute, at temperatures increasing from 25 degrees Celsius to 120 degrees Celsius at a rate of 3 degrees Celsius per minute with the 120 degree temperature being held for an hour. These catalysts were then reduced with flowing hydrogen at 90 cubic centimeters per minute, with the temperature being raised from 120 degrees Celsius to 220 degrees Celsius at 3 degrees per minute and the 220 degree temperature being held for 2 hours.

The reaction temperature was set at the same 220 degrees Celsius, with a reaction pressure of 20 pounds per square inch, gauge, a residence time of 3.5 seconds, a liquid hourly space velocity of 0.91 $hr^{-1}$ and a hydrogen to 1,2,3-trichloropropane (TCP) molar feed ratio of 6.0 to 1. Hydrogen chloride when added was metered in as a gas in a 3.0 to 1 molar ratio with respect to the 1,2,3-trichloropropane.

Selectivities to allyl chloride and to propylene, as well as percent conversion of the 1,2,3-trichloropropane, were assessed initially for all of the catalysts, and at a later period in time when the percent conversion reached 20 percent for the standard BPLF3 carbon-based catalyst as well as for the runs of the BPLF3 carbon-based catalyst involving HCl in the feed. The results are as indicated in Table 8:

hours. The catalyst "C" in Table 9 corresponds to this third catalyst sample.

Finally, a fourth catalyst sample was held under flowing

TABLE 8

| Catalyst | HCl/TCP in Feed | Initial (Pct.) | | | 20 Percent Conversion | | | Deactivation |
|---|---|---|---|---|---|---|---|---|
| | | TCP Conversion | Propylene Selectivity | Allyl Selectivity | Hrs. Online | Propylene Selectivity | Allyl Selectivity | Rate (Pct. Conv/Hr.) |
| 0.25 Pt/0.9 Cu//C (BPLF3) | 0 | 85 | 85 | 5 | 23 | 20 | 80 | 2.8 |
| 0.25 Pt/0.9 Cu//C (BPLF3) | 3 | 55 | 70 | 26 | 136 | 13 | 85 | 0.26 |
| 0.5 Pt/0.9 Cu//C (BPLF3) | 3 | 75 | 85 | 7 | — | — | — | 0.33 |
| 0.5 Pt/0.9 Cu//C (WSIV) | 0 | 25 | 85 | 5 | — | — | — | 0.4 |
| 0.5 Pt/0.9 Cu//C (PCB) | 0 | 30 | 65 | 3 | — | — | — | 0.4 |

EXAMPLES 18–21

These examples compare the effects on conversion and the selectivities to propylene and propane in a PDC to propylene process of pretreating a bimetallic platinum/copper catalyst by exposure to a chloride source (hydrogen chloride) without any reduction of the catalyst under hydrogen, of combining reduction under hydrogen with chloride source pretreatment, of using reduction without any chloride source pretreatment, and of starting up the dried catalyst without prior exposure to a chloride source or reduction. A quantity of catalyst was prepared according to the methods described in Examples 13–17 above, including 0.5 percent by weight of platinum and 0.9 percent by weight of copper on the Calgon BPLF3 carbon support.

Using the apparatus and basic procedures of Examples 11–12 and 13–17, a first catalyst sample was charged to the reactor and dried under flowing nitrogen at 90 cubic centimeters per minute, at temperatures increasing from 25 degrees Celsius to 120 degrees Celsius at a rate of 3 degrees Celsius per minute and with the 120 degree temperature being held for an hour. The catalyst was then reduced with flowing hydrogen at 90 cubic centimeters per minute, with the temperature being raised from 120 degrees Celsius to 235 degrees Celsius (instead of 220 degrees Celsius, as in Examples 13–17) at 3 degrees per minute and the 235 degree temperature being held for 2 hours. The catalyst prepared and treated in this fashion is catalyst "A" in Table 9 below.

A second sample was charged and dried from 25 degrees Celsius to 120 degrees Celsius under flowing nitrogen, as with the first sample. After holding at 120 degrees for one hour, however, a 50 cubic centimeter per minute flow of hydrogen chloride was introduced and maintained for one half hour. The temperature was then raised from 120 degrees to 235 degrees Celsius at 3 degrees per minute, under a reducing and chloride-source pretreating flow of 140 cc/min of a 2:1 mixture of hydrogen and hydrogen chloride. The resulting catalyst was held at 235 degrees for two hours, and is designated as catalyst "B" in Table 9 below.

A third catalyst sample was dried from 25 degrees Celsius to 235 degrees Celsius at a rise of 3 degrees Celsius per minute, under flowing nitrogen at 90 cc/min. After holding for 4 hours at 235 degrees Celsius, a flow of 50 cc/min. of pure HCl was begun and maintained over an additional 4 hours. The catalyst "C" in Table 9 corresponds to this third catalyst sample.

Finally, a fourth catalyst sample was held under flowing nitrogen (at 90 cc/min.) as the temperature was raised from 25 degrees Celsius to 235 degrees Celsius at 3 degrees per minute, and then maintained at 235 degrees for 3 hours. This catalyst is catalyst "D" in Table 9.

Reaction conditions for catalysts "A" and "B" were 235 degrees Celsius, 75 psig, a liquid hourly space velocity of 0.44 hr$^{-1}$, a residence time of 5 seconds and a hydrogen to PDC molar feed ratio of 3.0. Reaction conditions for catalysts "C" and "D" were somewhat different, in that the residence time was 10 seconds instead of 5 seconds and the hydrogen to PDC ratio was 1:1 instead of 3:1.

The selectivities to propylene, 2-chloropropane (2-CPa) and propane, as well as the percent of PDC converted, are as summarized in Table 9 for each of the catalysts A-D.

TABLE 9

| Catalyst | PDC Conversion (Pct.) | $C_3H_8$ Selectivity (Pct.) | $C_3H_6$ Selectivity (Pct.) | 2-CPa Selectivity (Pct.) |
|---|---|---|---|---|
| A | 68 | 48 | 40 | 12 |
| B | 67 | 2 | 86 | 12 |
| C | 26 | 0.25 | 84 | 13 |
| D | 32 | 0.42 | 86 | 11 |

EXAMPLE 22

The feedstock for this run was 1,1,2-trichloroethane. A 0.5 percent by weight of platinum, 0.9 percent by weight of copper on BPLF3 carbon catalyst was prepared, charged, dried, and reduced for use in this Example as in previous Examples. Using the apparatus of Examples 11-12, 1,1,2-trichloroethane was fed with hydrogen to the reactor in a 1:1 molar feed ratio and with a 5.0 second residence time, at 76 psig and 235 degrees Celsius. Eighty (80) percent of the 1,1,2-trichloroethane was observed to be converted initially to reaction products including vinyl chloride at 76 percent selectivity, ethylene at 14 percent selectivity, and ethane at 8 percent selectivity.

A second run was then conducted at a 3:1 molar feed ratio of hydrogen to 1,1,2-trichloroethane (other conditions being the same), with an initial conversion rate of 84 percent. Products were vinyl chloride at 86 percent selectivity, ethylene at 8 percent selectivity and ethane at 5.5 percent selectivity.

EXAMPLE 23

The apparatus and procedures of Example 22 were used with a feedstock of 1,1,1,2-tetrachloroethane, except that the molar feed ratio of hydrogen to 1,1,1,2-tetrachloroethane was set at 1.6:1 and the residence time was 4.0 seconds instead of 5.0. Virtually all of the 1,1,1,2-tetrachloroethane (99.95 percent) was initially converted to reaction products including vinylidene chloride at 93 percent selectivity, vinyl chloride at 1 percent selectivity, trichloroethylene at 3 percent, and ethane and ethylene at 3 percent combined. Catalytic activity declined fairly rapidly thereafter due (it is believed) to polymerization of the vinylidene chloride on the catalyst.

EXAMPLE 24

The methods and apparatus of Examples 11–12 were employed for converting trichloroethylene to reaction products including ethane over a catalyst of 0.24 percent by weight of platinum and 1.37 percent by weight of gold on the BPLF3 carbon support. The catalyst was prepared from a solution of $H_2PtCl_6 \cdot H_2O$ and $HAuCl_4 \cdot H_2O$ in water, and to which the BPLF3 carbon had been added. The catalyst was then dried, charged and reduced under flowing hydrogen as in Examples 11–12.

At a reaction temperature of 235 degrees Celsius, a pressure of 76 psig, a 4.9 second residence time, and a molar feed ratio of hydrogen to vaporized trichloroethylene of 2.75, there was a 75 percent conversion of trichloroethylene to reaction products including ethane at 80 percent selectivity, ethylene (16 percent selectivity), cis-1,2-dichloroethylene (2 percent) and vinyl chloride, ethyl chloride, vinylidene chloride, trans-1,2-dichloroethylene and 1,2-dichloroethane (or EDC) at less than 1 percent total.

EXAMPLE 25

The same catalyst, procedures and apparatus were used as in Example 24, but at a reaction temperature of 235 degrees Celsius, a pressure of 76 psig, a residence time of 4.9 seconds and a molar feed ratio of hydrogen to trichloroethylene of 5.5. After 23 hours on line, trichloroethylene conversion was at 93 percent, with ethane being produced therefrom at a selectivity of 96 percent, ethylene at 2 percent, cis-1,2-dichloroethylene at 0.5 percent, and vinyl chloride and the other minor products of Example 1 being produced at a selectivity of less than 0.5 percent.

EXAMPLES 26–30

For these examples, the same apparatus and procedures were generally employed as in Examples 11–12 above to evaluate and compare several different catalyst combinations for converting PDC to propylene. Each of these catalysts was prepared from a solution in water of the chlorides of the metals involved, and using the Calgon BPLF3 activated carbon. The catalysts were each charged, air- and oven-dried, and reduced with hydrogen in the manner of Examples 1–10.

The reaction temperature for this comparison was 220 degrees Celsius, the pressure was atmospheric, the residence time was 1 second, and the molar feed ratio of hydrogen to PDC was set at 3:1.

The percent conversions and the selectivities to various products (in percent) from these runs are provided in Table 10, wherein "2-CPA" is 2-chloropropane:

TABLE 10

| Catalyst | Conversion | $C_3H_6$ | $C_3H_8$ | 2-CPA |
| --- | --- | --- | --- | --- |
| 0.25 Pt/0.25 Rh/1.3 Cu | 29 | 86 | 13 | 1 |
| 0.25 Pt/0.13 Ru/0.9 Cu | 37 | 98 | 1 | 1 |
| 0.26 Ru/0.9 Cu | 12 | 95 | 3 | 1 |
| 0.5 Rh/1.7 Cu | 19 | 95 | 3 | 1 |
| 0.5 Pd/1.6 Cu | 24 | 95 | 1 | 4 |

EXAMPLES 31–45

Examples 31–45 below focus on the dechlorination of 1,2-dichloropropane over various supported bimetallic catalysts having the same atomic metal ratios of the hydrogenating metal and surface segregating metal, with the catalysts each having been prepared by coimpregnation from an aqueous solution of the chloride salts of the metals involved on the Calgon BPLF3 activated carbon, air-drying for eighteen hours at ambient temperatures, then oven-drying for 2 hours at 120 degrees Celsius.

A catalyst charge as thus prepared (0.6 grams in each of Examples 31–45) was then generally placed in a tubular reactor (comprised of Monel™ nickel alloy (unless specifically noted below all of the components, tubing and fittings of the test reactor apparatus were also made of Monel™ nickel alloy (Huntington Alloys, Inco Alloys International, Inc.), having a diameter (O.D.) of ½ inch (1.27 cm), and being 12 inches (30.5 cm) in length and located within an aluminum block heated by a cartridge heater and regulated via a computer to maintain a selected reaction temperature of 220 degrees Celsius) over a glass wool support contained in the center of the reactor tubing.

The catalyst was then covered with a plug of glass wool and dried for from 1 to 24 hours at 120 degrees Celsius under a nitrogen purge. The catalyst was then reduced by passing hydrogen through the reactor at a flow rate of 90 mL/minute for from 1 to 24 hours. The reaction temperature of 220 degrees Celsius was achieved, and the reaction temperature and hydrogen gas flow were allowed to equilibrate for about 1 hour before the liquid PDC feedstock flow was started into the apparatus.

In each instance, PDC was pumped via a high pressure syringe pump through 1.6 mm (O.D.) (¹⁄₁₆ inch) Monel™ nickel alloy tubing into a packed sample cylinder serving as a feed evaporator.

The ¹⁄₁₆th inch tubing extended almost to the center of the packed cylinder, which was heated to a vaporizing temperature of 180 degrees Celsius using electrical heat tracing. Vaporization of the PDC feedstock was accomplished in the feed line, so that the PDC was superheated when combined with the hydrogen feed stream. Thermocouples were used to monitor the skin temperature of the feed evaporator and the temperature of the gas exiting the feed evaporator, and the temperature of the feed evaporator was controlled by computer.

The hydrogen feed stream was metered (at a 3 to 1 molar ratio of hydrogen to PDC) to a preheater using a Model 8249 linear mass flow controller from Matheson Gas Products, Inc. Secaucus, N.J., with the preheater consisting of a packed sample cylinder wrapped with electrical heat tracing. Thermocouples were used to monitor both the skin temperature of the preheater and the temperature of the gas exiting the preheater. The preheater temperature was set and maintained at 140 degrees Celsius.

Vaporized PDC exiting the evaporator was mixed with the hydrogen gas from the preheater in a 2 foot (0.61 meter) long section of ¼ inch (0.64 cm) tubing maintained at a temperature of 140 degrees Celsius. The mixed gases then were passed into and reacted within the tubular reactor at the aforementioned reaction temperature of 220 degrees Celsius, under atmospheric pressure, with a 3:1 molar feed ratio of hydrogen to PDC and a 1 second residence time.

After reacting the PDC and hydrogen in the vapor phase in the tubular reactor thus prepared, the products from the reaction were passed to a gas sampling valve, which provided gaseous aliquots for online gas chromatographic analysis in a Hewlett-Packard Model 5890 Series II gas chromatograph (Hewlett-Packard Company). The gas chromatograph was equipped with a flame ionization detector, and used 30 meter by 0.53 millimeter (I.D.) 100 percent methyl silicone/fused silica and 30 meter by 0.53 millimeter (I.D.) porous polymer-lined fused silica columns to separate the various reaction products. Response factors were conventionally determined by injections of gravimetrically-prepared standards of the individual reaction products. These response factors were applied in conjunction with individual peak areas and the total mols of all reaction products to determine the mol percents of individual components in the reactor effluent, and the selectivity to individual reaction products.

The results from Examples 31–45 are reported in Table 11 below:

TABLE 11

| HM/SSM[a] (Wt. Pct.) | PDC Conversion (Pct.) | $C_3H_6$ Selectivity (Pct.) | $C_3H_8$ Selectivity (Pct.) |
| --- | --- | --- | --- |
| 0.5 Pt/2.0 La | 2 | 28 | 43 |
| 0.5 Pt/0.7 Ti | 2 | 59 | 24 |
| 0.5 Pt/0.7 V | 8 | 22 | 75 |
| 0.5 Pt/0.7 Cr | 30 | 3 | 96 |
| 0.5 Pt/0.8 Mn | 40 | 2 | 98 |
| 0.5 Pt/0.8 Fe | 85 | 1 | 99 |
| 0.5 Pt/0.8 Co | 30 | 3 | 96 |
| 0.5 Pt/0.9 Ni | 38 | 38 | 60 |
| 0.5 Pt/0.9 Cu | 32 | 97 | 1 |
| 0.5 Pt/0.9 Zn | 30 | 3 | 96 |
| 0.5 Pd/1.7 Zn | 22 | 53 | 33 |
| 0.5 Pd/2.9 Cd | 12 | 92 | 2 |
| 0.5 Pt/1.6 In | 1 | 41 | 47 |
| 0.5 Pt/1.7 Sn | 25 | 96 | 1 |
| 0.5 Pt/2.9 Bi | 5 | 92 | 1 |

[a]HM = hydrogenating metal component; SSM = surface segregating component.

While various embodiments of the processes and catalysts of the present invention have been described and/or exemplified herein, those skilled in the art will readily appreciate that numerous changes can be made thereto which are nevertheless properly considered to be within the scope or spirit of the present invention as more particularly defined by the claims below.

What is claimed is:

1. A process for the conversion of a chlorinated alkane feedstock containing two or more chlorines to reaction products comprising a less chlorinated alkene, wherein the chlorinated alkane feedstock is reacted with hydrogen in the presence of a supported catalyst consisting essentially of an active hydrogenating metal component selected from the Group VIb and Group VIII metals in elemental or compound form and a surface segregating metal component selected from the metals of Groups IB, IIB, IIIA, IIIB, IVA, IVB, VA, VB, VIA, VIIA and VIII in elemental or compound form on a support, the group VIII hydrogenating metal component being different from the group VIII metal comprising the surface segregating metal component under conditions effective to produce the corresponding less chlorinated alkene in a yield of at least about 10 percent and in preference to a corresponding less-chlorinated alkane.

2. A process as defined in claim 1, wherein hydrogen chloride is incorporated in the feed to the process.

3. A process as defined in claim 1, wherein the less chlorinated alkene is produced at a yield of at least 20 percent.

4. A process as defined in claim 3, wherein the less chlorinated alkene is produced at a yield of at least 30 percent.

5. A process as defined in claim 1, wherein the catalyst consists of said active hydrogenating metal component and said surface segregating metal component on a support.

6. A process as defined in claim 5, wherein the catalyst consists of one or more Group IB surface segregating metals in elemental or compound form and of one or more active Group VIII hydrogenating metals in elemental or compound form on the support.

7. A process as defined in claim 6, wherein the one or more Group IB metals comprise copper and wherein the one or more Group VIII metals comprise platinum.

8. A process as defined in claim 7, wherein the Group IB and Group VIII metals in the catalyst consist substantially entirely of copper and platinum.

9. A process as defined in claim 8, wherein the Group IB and Group VIII metals consist of copper and platinum.

10. A process as defined in claim 1, wherein the catalyst consists essentially of one or more Group IB surface segregating metals in elemental or compound form and of one or more active Group VIII hydrogenating metals in elemental or compound form on the support.

11. A process as defined in claim 10, wherein the one or more Group IB metals include copper and wherein the one or more Group VIII metals include platinum.

12. A process as defined in claim 11, wherein the Group IB and Group VIII metals in the catalyst consist substantially entirely of copper and platinum.

13. A process as defined in claim 12, wherein the Group IB and Group VIII metals consist of copper and platinum.

14. A process as defined in claim 1, wherein:

the chlorinated alkane feedstock is 1,2-dichloropropane; and the catalyst is a supported bimetallic catalyst containing from about 0.01 to about 5.0 percent by weight of platinum on an elemental basis and from 0.01 to about 15 percent by weight of copper, also on an elemental basis, and the catalyst support is a carbon having a specific surface area of at least about 200 $m^2/g$.

15. A process as defined in claim 14, wherein the catalyst contains about 0.10 to about 3.0 percent by weight of platinum on an elemental basis and from about 0.05 to about 5 percent by weight of copper, also on an elemental basis, and the catalyst support is a carbon having a specific surface area of at least about 500 $m^2/g$.

16. A process as defined in claim 15, wherein the catalyst contains about 0.20 to about 1.0 percent by weight of platinum on an elemental basis and from about 0.1 to about 2.0 percent by weight of copper, also on an elemental basis, and the catalyst support is a carbon having a specific surface area of at least about 800 $m^2/g$.

17. A process as defined in claim 14, wherein the catalyst has been pretreated by exposure to a chloride source.

18. A process as defined in claim 15, wherein the catalyst has been pretreated by exposure to a chloride source.

19. A process as defined in claim 16, wherein the catalyst has been pretreated by exposure to a chloride source.

20. A process as defined in any one of claims 14–19, wherein the reaction is conducted in the gas phase at a pressure of from atmospheric pressure to about 1500 psig, at a temperature of from about 100 degrees Celsius to about 350 degrees Celsius, a residence time of from about 0.25 seconds to about 180 seconds, and a hydrogen to 1,2-dichloropropane molar feed ratio of from about 0.1:1 to about 100:1.

21. A process as defined in any one of claims 14–19, wherein the reaction is conducted in the gas phase at a pressure of from about 5 psig to about 500 psig, at a temperature of from about 180 degrees Celsius to about 300 degrees Celsius, a residence time of from about 1.0 seconds to about 20 seconds, and a hydrogen to 1,2-dichloropropane molar feed ratio of from about 0.3:1 to about 10:1.

22. A process as defined in any of claims 14–19, wherein the reaction is conducted in the gas phase at a pressure of from about 50 psig to about 300 psig, at a temperature of from about 200 degrees Celsius to about 260 degrees Celsius, a residence time of from about 5 seconds to about 15 seconds, and a hydrogen to 1,2-dichloropropane molar feed ratio of from about 0.5:1 to about 3:1.

23. A process as defined in claim 1, wherein the chlorinated alkane feedstock is 1,2-dichloropropane, and wherein the catalyst and process conditions are sufficient to produce propylene at a yield of at least about 15 percent.

24. A process as defined in claim 23, wherein the catalyst and process conditions are sufficient to produce propylene at a yield of at least about 35 percent.

25. A process as defined in claim 1, wherein the chlorinated alkane feedstock is 1,2,3-trichloropropane and one or both of allyl chloride and propylene are produced.

26. A process as defined in claim 1, wherein the chlorinated alkane feedstock is 1,1,1,2-tetrachloroethane and the corresponding less chlorinated alkene product is vinylidene chloride.

27. A process as defined in claim 1, wherein the chlorinated alkane feedstock is 1,1,2-trichloroethane and one or both of vinyl chloride and ethylene are produced.

* * * * *